US005770603A

United States Patent [19]
Gibson

[11] Patent Number: 5,770,603
[45] Date of Patent: Jun. 23, 1998

[54] QUINAZOLINE DERIVATIVES

[75] Inventor: Keith Hopkinson Gibson, Macclesfield, United Kingdom

[73] Assignee: Zeneca Limited, London, United Kingdom

[21] Appl. No.: 871,989

[22] Filed: Apr. 10, 1997

[30] Foreign Application Priority Data

Apr. 13, 1996 [GB] United Kingdom .................. 9607729

[51] Int. Cl.[6] ........................ A61K 31/495; A61K 31/50; C07D 403/02; C07D 403/14
[52] U.S. Cl. ............................................ 514/259; 544/293
[58] Field of Search ............................. 544/293; 514/259

[56] References Cited

U.S. PATENT DOCUMENTS

| | | | |
|---|---|---|---|
| 3,266,990 | 8/1966 | Lutz et al. | 514/259 |
| 4,343,940 | 8/1982 | Kreighbaum et al. | 514/259 |
| 5,457,105 | 10/1995 | Barker | 514/234.5 |
| 5,475,001 | 12/1995 | Barker | 514/258 |
| 5,580,870 | 12/1996 | Barker et al. | 514/234.5 |
| 5,616,582 | 4/1997 | Barker | 514/234.5 |

FOREIGN PATENT DOCUMENTS

| | | |
|---|---|---|
| 0 326 307 | 2/1989 | European Pat. Off. . |
| 0 326 330 A2 | 8/1989 | European Pat. Off. . |
| 0 520 722 A1 | 12/1992 | European Pat. Off. . |
| 0 566 226 A1 | 10/1993 | European Pat. Off. . |
| 0 602 851 A1 | 6/1994 | European Pat. Off. . |
| 0 635 498 A1 | 1/1995 | European Pat. Off. . |
| 0 635 507 A1 | 1/1995 | European Pat. Off. . |
| 0 682 027 A1 | 11/1995 | European Pat. Off. . |
| 2 033 894 | 5/1980 | United Kingdom . |
| 2 160 201 | 12/1985 | United Kingdom . |
| WO 97/13760 | 4/1977 | WIPO . |
| WO 92/14716 | 9/1992 | WIPO . |
| WO 92/20642 | 11/1992 | WIPO . |
| WO 95/06648 | 3/1995 | WIPO . |
| WO 95/15758 | 6/1995 | WIPO . |
| WO 95/15952 | 6/1995 | WIPO . |
| WO 95/19169 | 7/1995 | WIPO . |
| WO 95/19774 | 7/1995 | WIPO . |
| WO 95/19970 | 7/1995 | WIPO . |
| WO 95/21613 | 8/1995 | WIPO . |
| WO 95/23141 | 8/1995 | WIPO . |
| WO 95/24190 | 9/1995 | WIPO . |
| WO 96/07657 | 3/1996 | WIPO . |
| WO 96/09294 | 3/1996 | WIPO . |
| WO 96/15118 | 5/1996 | WIPO . |
| WO 96/16960 | 6/1996 | WIPO . |
| WO 96/29331 | 9/1996 | WIPO . |
| WO 96/30347 | 10/1996 | WIPO . |
| WO 96/31510 | 10/1996 | WIPO . |
| WO 96/33977 | 10/1996 | WIPO . |
| WO 96/33978 | 10/1996 | WIPO . |
| WO 96/33979 | 10/1996 | WIPO . |
| WO 96/33980 | 10/1996 | WIPO . |
| WO 96/33981 | 10/1996 | WIPO . |
| WO 96/34867 | 11/1996 | WIPO . |
| WO 96/35689 | 11/1996 | WIPO . |
| WO 96/39145 | 12/1996 | WIPO . |
| WO 96/40142 | 12/1996 | WIPO . |
| WO 96/40648 | 12/1996 | WIPO . |
| WO 97/02266 | 1/1997 | WIPO . |
| WO 97/3069 | 1/1997 | WIPO . |
| WO 97/13771 | 4/1997 | WIPO . |

OTHER PUBLICATIONS

Rewcastle et al., "Tyrosine Kinase Inhibitors. 5. Synthesis and Structure–Activity Relationships for 4–[(Phenylmethyl)amino]– and 4–(Phenylamino)quinazolines as Potent Adenosine 5'–Triphosphate Binding Site Inhibitors of the Tyrosine Kinase Domain of the Epidermal Growth Factor Receptor", J.Med.Chem. 1995, vol. 38, pp. 3482–3487.

Burke, Jr., "Protein–tyrosine kinase inhibitors," Drugs of the Future 1992, vol. 17(2), pp. 119–131.

Spence, "Inhibitors of Tyrosine Kinase Activity as Anticancer Therapeutics: Recent Developments," Expert Opinion in Therapeutic Patents, Jan. 1993, Patent Update, Anticancers, etc., pp. 3–9, Current Drugs Ltd. ISSN 0962–2594.

Spada, et al., Small molecule inhibitors of tyrosine Kinase activity, Exp.Opin.Ther.Patents (1995), 5(8):805–817, Patent Update, Oncologic, Endocrine & Metabolic, Ashley Publications Ltd ISSN 1354–3776.

Bridges, "The current status of tyrosine kinase inhibitors: do the diarylamine inhibitors of the EGF receptor represent a new beginning?," Exp.Opin.Ther.Patents (1995), 5(12): 1245–1257, Editorial, Oncologic, Endocrine & Metabolic, 1995 Ashley Publications Ltd. ISSN 1354–3776.

Traxler, et al., "Recent advances in protein typrosine kinase inhibitors," Drugs of the Future 1995, vol. 20(12, pp. 1261–1274.

(List continued on next page.)

Primary Examiner—Matthew V. Grumbling

[57] ABSTRACT

The invention concerns quinazoline derivatives of the formula I

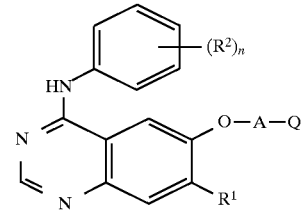

wherein n is 1,2 or 3 and each $R^2$ is independently halogeno, trifluoromethyl or (1-4C)alkyl;

$R^1$ is (1-4C)alkoxy;

A is (1-4C)alkylene; and

Q is a saturated, monocyclic 4-, 5-, 6- or 7-membered heterocyclic ring containing one or two oxygen heteroatoms, which ring optionally bears up to four (1-4C)alkyl substituents; or a pharmaceutically-acceptable salt thereof;

processes for their preparation, pharmaceutical compositions containing them and the use of their receptor tyrosine kinase inhibitory properties in the treatment of proliferative disease such as cancer.

10 Claims, No Drawings

OTHER PUBLICATIONS

Iyer, et al., "Studies In Potential Amoebicides: Part III—Synthesis of ₄–Substituted Amino–8–Hydroxy) Quinazolines & ₃–Substituted 8–Hydroxy(&8–Methody)–₄–Quinazolones," J.Sci.Industr.Res., vol. 15C, Jan. 1956, pp. 1–7.

Derwent Abstract 82–87077, vol. 6, No. 244, Dec. 1982, JP 57–144266, Kobayashi, Sep. 1982, "4–Anilinoquinazoline Derivative, its Preparation and Analgesic and Antiphlogistic Agent Containing Said Derivative as Active Component".

Derwent Abstract 81–28290, JP 56–20577, Feb. 1981, Sankyo and Ube, "4–(N–alkyl:anilino) quinazoline derivs . . . having analgesic and antiinflammatory actions".

Derwent Abstract 84–53835, JP 59–13765, Jan. 1984, Kyorin, "2–(4–Quinazolinyl)amino benzoic acid derivs . . . having analgesic and antiinflammatory activities".

Chem.Abs., vol. 92:76445u, 1980, pp. 674–675, Li, et al.

Chem.Abs., vol. 96:122728w, 1982, p. 695, Lin et al.

Fry et al., "A Specific Inhibitor of the Epidermal Growth Factor Receptor Tyrosine Kinase," Science, vol. 265, Aug. 19, 1994, pp. 1093–1095.

Buchdunger, et al., "4,5–Dianilinophthalimide: A protein–tyrosine kinase inhibitor with selectivity for the epidermal growth factor receptor signal transduction pathway and potent in vivo antitumor activity," Proc.Natl.Acad.Sci., USA, vol. 91, pp. 2334–2338, Mar. 1994, Applied Biological Sciences.

Trinks, et al., "Dianilinophthalimides: Potent and Selective, ATP–Competitive Inhibitors of the EGF–Receptor Protein Tyrosine Kinase," J.Med. Chem. 1994, vol. 37, pp. 1015–1027.

Maguire, et al., "A New Series of PDGF Receptor Tyrosine Kinase Inhibitors: 3–Substituted Quinoline Derivatives,", J.Med.Chem. 1994, vol. 37, pp. 2129–2137.

Dolle, et al., "5,7–Dimethoxy–3–(4–pyridinyl)quinoline is a Potent and Selective Inhibitor of Human Vascular β–Type Platelet–Derived Growth Factor Receptor Tyrosine Kinase," J.Med.Chem. 1994, vol. 37, pp. 2627–2629.

Bridges, et al., "Enantioselective Inhibition of the Epidermal Growth Factor Receptor Tyrosine Kinase by 4–(α–Phenethylamino)quinazolines," Bioorganic & Medicinal Chemistry, vol. 3, No. 12, pp. 1651–1656, 1995.

Ward, et al., "Epidermal Growth Factor Receptor Tyrosine Kinase—Investigation of Catalytic Mechanism, Structure–Based Searching and Discovery of a Potent Inhibitor," Biochem.Pharmacology, vol. 48, No. 4, pp. 659–666 (1994).

QUINAZOLINE DERIVATIVES

The invention relates to quinazoline derivatives, or pharmaceutically-acceptable salts thereof, which possess anti-proliferative activity such as anti-cancer activity and are accordingly useful in methods of treatment of the human or animal body. The invention also relates to processes for the manufacture of said quinazoline derivatives, to pharmaceutical compositions containing them and to their use in the manufacture of medicaments of use in the production of an anti-proliferative effect in a warm-blooded animal such as man.

Many of the current treatment regimes for cell proliferation diseases such as psoriasis and cancer utilise compounds which inhibit DNA synthesis. Such compounds are toxic to cells generally but their toxic effect on rapidly dividing cells such as tumour cells can be beneficial. Alternative approaches to anti-proliferative agents which act by mechanisms other than the inhibition of DNA synthesis have the potential to display enhanced selectivity of action.

In recent years it has been discovered that a cell may become cancerous by virtue of the transformation of a portion of its DNA into an oncogene i.e. a gene which, on activation, leads to the formation of malignant tumour cells (Bradshaw, Mutagenesis, 1986, 1, 91). Several such oncogenes give rise to the production of peptides which are receptors for growth factors. The growth factor receptor complex subsequently leads to an increase in cell proliferation. It is known, for example, that several oncogenes encode tyrosine kinase enzymes and that certain growth factor receptors are also tyrosine kinase enzymes (Yarden et al., Ann. Rev. Biochem., 1988, 57, 443; Larsen et al. Ann. Reports in Med. Chem. 1989, Chpt. 13).

Receptor tyrosine kinases are important in the transmission of biochemical signals which initiate cell replication. They are large enzymes which span the cell membrane and possess an extracellular binding domain for growth factors such as epidermal growth factor (EGF) and an intracellular portion which functions as a kinase to phosphorylate tyrosine amino acids in proteins and hence to influence cell proliferation. Various classes of receptor tyrosine kinases are known (Wilks, Advances in Cancer Research, 1993, 60, 43–73) based on families of growth factors which bind to different receptor tyrosine kinases. The classification includes Class I receptor tyrosine kinases comprising the EGF family of receptor tyrosine kinases such as the EGF, TGFα, NEU, erbB, Xmrk, HER and let23 receptors, Class II receptor tyrosine kinases comprising the insulin family of receptor tyrosine kinases such as the insulin, IGFI and insulin-related receptor (IRR) receptors and Class III receptor tyrosine kinases comprising the platelet-derived growth factor (PDGF) family of receptor tyrosine kinases such as the PDGFα, PDGFβ and colony-stimulating factor 1 (CSF1) receptors. It is known that Class I kinases such as the EGF family of receptor tyrosine kinases are frequently present in common human cancers such as breast cancer (Sainsbury et al., Brit. J. Cancer, 1988, 58, 458; Guerin et al., Oncogene Res., 1988, 3, 21 and Klijn et al., Breast Cancer Res. Treat., 1994, 29, 73), non-small cell lung cancers (NSCLCs) including adenocarcinomas (Cerny et al., Brit. J. Cancer, 1986, 54, 265; Reubi et al., Int. J. Cancer, 1990, 45, 269; and Rusch et al., Cancer Research 1993, 53, 2379) and squamous cell cancer of the lung (Hendler et al., Cancer Cells, 1989, 7, 347), bladder cancer (Neal et al. Lancet, 1985, 366), oesophageal cancer (Mukaida et al., Cancer, 1991, 68, 142), gastrointestinal cancer such as colon, rectal or stomach cancer (Bolen et al., Oncogene Res., 1987, 1, 149), cancer of the prostate (Visakorpi et al. Histochem. J., 1992, 24, 481), leukaemia (Konaka et al., Cell 1984, 37, 1035) and ovarian, bronchial or pancreatic cancer (European Patent Specification No. 0400586). As further human tumour tissues are tested for the EGF family of receptor tyrosine kinases it is expected that their widespread prevalance will be established in further cancers such as thyroid and uterine cancer. It is also known that EGF type tyrosine kinase activity is rarely detected in normal cells whereas it is more frequently detectable in malignant cells (Hunter, Cell, 1987, 50, 823). It has been shown more recently (W J Gullick, Brit. Med. Bull., 1991, 47, 87) that EGF receptors which possess tyrosine kinase activity are overexpressed in many human cancers such as brain, lung squamous cell, bladder, gastric, breast, head and neck, oesophageal, gynaecological and thyroid tumours.

Accordingly it has been recognised that an inhibitor of receptor tyrosine kinases should be of value as a selective inhibitor of the growth of mammalian cancer cells (Yaish et al. Science, 1988, 242, 933). Support for this view is provided by the demonstration that erbstatin, an EGF receptor tyrosine kinase inhibitor, specifically attenuates the growth in athymic nude mice of a transplanted human mammary carcinoma which expresses EGF receptor tyrosine kinase but is without effect on the growth of another carcinoma which does not express EGF receptor tyrosine kinase (Toi et al., Eur. J. Cancer Clin. Oncol., 1990, 26, 722.) Various derivatives of styrene are also stated to possess tyrosine kinase inhibitory properties (European Patent Application Nos. 0211363, 0304493 and 0322738) and to be of use as anti-tumour agents. The in vivo inhibitory effect of two such styrene derivatives which are EGF receptor tyrosine kinase inhibitors has been demonstrated against the growth of human squamous cell carcinoma inoculated into nude mice (Yoneda et al, Cancer Research, 1991, 51, 4430). Various known tyrosine kinase inhibitors are disclosed in a more recent review by T R Burke Jr. (Drugs of the Future, 1992, 17, 119).

It is now known from European Patent Applications Nos. 0520722, 0566226 and 0635498 and from International Patent Applications WO 95/15758, WO 95/19169, WO 96/09294, WO 96/15118, WO 96/16960 and WO 96/30347 that certain quinazoline derivatives which bear an anilino substituent at the 4-position possess receptor tyrosine kinase inhibitory activity. It is further now known from European Patent Application No. 0602851 and from International Patent Application WO 95/23141 that certain quinazoline derivatives which bear a heteroarylamino substituent at the 4-position also possess receptor tyrosine kinase inhibitory activity.

It is further known from International Patent Application WO 92/20642 that certain aryl and heteroaryl compounds inhibit EGF and/or PDGF receptor tyrosine kinase. There is the disclosure of certain quinazoline derivatives therein but no mention is made of 4-anilinoquinazoline derivatives.

The in vitro anti-proliferative effect of a 4-anilinoquinazoline derivative has been disclosed by Fry et al., Science, 1994, 265, 1093. It was stated that the compound 4-(3'-bromoanilino)-6, 7-dimethoxyquinazoline was a highly potent inhibitor of EGF receptor tyrosine kinase.

The in vivo inhibitory effect of a 4,5-dianilinophthalimide derivative which is an inhibitor of the EGF family of receptor tyrosine kinases has been demonstrated against the growth in BALB/c nude mice of a human epidermoid carcinoma A-431 or of a human ovarian carcinoma SKOV-3 (Buchdunger et al., Proc. Nat. Acad. Sci., 1994, 91, 2334).

It is further now known from European Patent Application No. 0635507 and from International Patent Applications WO 95/06648, WO 95/19970 and WO 96/29331 that certain tricyclic compounds which comprise a 5- or 6-membered ring fused to the benzo-ring of a quinazoline possess receptor tyrosine kinase inhibitory activity or phosphodiesterase inhibitory activity. It is also known from European Patent Application No. 0635498 that certain quinazoline derivatives which carry an amino group at the 6-position and a halogeno group at the 7-position possess receptor tyrosine kinase inhibitory activity.

It is further now disclosed in International Patent Applications WO 96/33977, WO 96/33978, WO 96/33979, WO 96/33980 and WO 96/33981 that certain further quinazoline derivatives which bear an anilino substituent at the 4-position possess receptor tyrosine kinase inhibitory activity.

Accordingly it has been indicated that Class I receptor tyrosine kinase inhibitors will prove to be useful in the treatment of a variety of human cancers.

EGF type receptor tyrosine kinases have also been implicated in non-malignant proliferative disorders such as psoriasis (Elder et al., Science, 1989, 243, 811). It is therefore expected that inhibitors of EGF type receptor tyrosine kinases will be useful in the treatment of non-malignant diseases of excessive cellular proliferation such as psoriasis (where TGFα is believed to be the most important growth factor), benign prostatic hypertrophy (BPH), atherosclerosis and restenosis.

There is no disclosure in these documents of quinazoline derivatives which bear at the 4-position an anilino substituent and which also bear an alkoxy substituent at the 7-position and an oxygen-containing-heterocyclyl-alkoxy substituent at the 6-position. We have now found that such compounds possess potent anti-proliferative properties which are believed to arise from their Class I (EGF type) receptor tyrosine kinase inhibitory activity.

According to the present invention there is provided a quinazoline derivative of the formula I

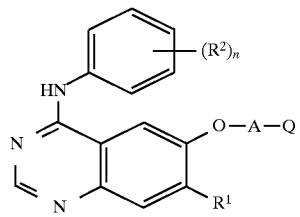

wherein n is 1,2 or 3 and each $R^2$ is independently halogeno, trifluoromethyl or (1-4C)alkyl;

$R^1$ is (1-4C)alkoxy;

A is (1-4C)alkylene; and Q is a saturated, monocyclic 4-, 5-, 6- or 7-membered heterocyclic ring containing one or two oxygen heteroatoms, which ring optionally bears up to four (1-4C)alkyl substituents; or a pharmaceutically-acceptable salt thereof.

In this specification the term "alkyl" includes both straight and branched chain alkyl groups but references to individual alkyl groups such as "propyl" are specific for the straight chain version only. An analogous convention applies to other generic terms.

Within the present invention it is to be understood that, insofar as certain of the compounds of the formula I may exist in optically active or racemic forms by virtue of one or more substituents containing an asymmetric carbon atom, the invention encompasses any such optically active or racemic form which possesses anti-proliferative activity.

The synthesis of optically active forms may be carried out by standard techniques of organic chemistry well known in the art, for example by synthesis from optically active starting materials or by resolution of a racemic form.

It is also to be understood that certain quinazoline derivatives of the formula I can exist in solvated as well as unsolvated forms such as, for example, hydrated forms. It is to be understood that the invention encompasses all such solvated forms which possess anti-proliferative activity.

The quinazolines of the formula I are unsubstituted at the 2-, 5- and 8-positions.

Suitable values for the generic radicals referred to above include those set out below.

A suitable value for $R^2$ when it is halogeno is, for example, fluoro, chloro, bromo or iodo; and when it is (1-4C)alkyl is, for example, methyl, ethyl, propyl, isopropyl or butyl.

A suitable value for $R^1$ when it is (1-4C)alkoxy is, for example, methoxy, ethoxy, propoxy, isopropoxy or butoxy.

A suitable value for A when it is (1-4C)alkylene is, for example, methylene, ethylene, 1-methylmethylene, trimethylene, 1-methylethylene, 2-methylethylene, 1,1-dimethylmethylene, tetramethylene, 1,1-dimethylethylene, 1,2-dimethylethylene, 2,2-dimethylethylene or 2-methyltrimethylene.

A suitable value for Q when it is a saturated, monocyclic 4-, 5-, 6- or 7-membered heterocyclic ring containing one or two oxygen heteroatoms is, for example, 2-oxetanyl, 3-oxetanyl, 2-tetrahydrofuranyl, 3-tetrahydrofuranyl, 1,3-dioxolan-2-yl, 1,3-dioxolan-4-yl, 1,3-dioxan-2-yl, 1,3-dioxan-4-yl, 1,3-dioxan-5-yl, 1,4-dioxan-2yl or 1,3-dioxepan-2-yl.

A suitable value for a (1-4C)alkyl substituent which may optionally be present on the heterocyclic ring Q is, for example, methyl, ethyl, propyl, isopropyl or butyl.

A suitable pharmaceutically-acceptable salt of a quinazoline derivative of the invention is, for example, an acid-addition salt of a quinazoline derivative of the invention which is sufficiently basic, for example, a mono- or di-acid-addition salt with, for example, an inorganic or organic acid, for example hydrochloric, hydrobromic, sulphuric, phosphoric, trifluoroacetic, citric, maleic, tartaric, fumaric, methanesulphonic or 4-toluenesulphonic acid.

Particular novel compounds of the invention include, for example, quinazoline derivatives of the formula I, or pharmaceutically-acceptable salts thereof, wherein:

(a) n is 1,2 or 3 and each $R^2$ is independently fluoro, chloro, bromo, trifluoromethyl or methyl; and $R^1$, A and Q have any of the meanings defined hereinbefore or in this section relating to particular novel compounds of the invention;

(b) n is 1,2 or 3 and each $R^2$ is independently fluoro, chloro or bromo; and $R^1$, A and Q have any of the meanings defined hereinbefore or in this section relating to particular novel compounds of the invention;

(c) $R^1$ is methoxy or ethoxy; and n, $R^2$, A and Q have any of the meanings defined hereinbefore or in this section relating to particular novel compounds of the invention;

(d) A is methylene, ethylene or trimethylene; and n, $R^2$, $R^1$ and Q have any of the meanings defined hereinbefore or in this section relating to particular novel compounds of the invention;

(e) Q is a saturated, monocyclic 4-, 5- or 6-membered heterocyclic ring containing one or two oxygen heteroatoms; and n, $R^2$, $R^1$ and A have any of the meanings defined hereinbefore or in this section relating to particular novel compounds of the invention; and (f) Q is 2-oxetanyl, 3-oxetanyl, 2-tetrahydrofuranyl, 3-tetrahydrofuranyl, 1,3-dioxolan-2-yl, 1,3-dioxolan-4-yl, 1,3-dioxan-2-yl, 1,3-dioxan-4-yl or 1,3-dioxan-5yl; and n, $R^2$, $R^1$ and A have any of the meanings defined hereinbefore or in this section relating to particular novel compounds of the invention.

A preferred compound of the invention is a quinazoline derivative of the formula I wherein $(R^2)_n$ is 3'-chloro, 3'-bromo, 3',4'-difluoro, 3',4'-dichloro, 3'-fluoro-4'-chloro or 3'-chloro-4'-fluoro;

R' is methoxy or ethoxy;

A is methylene, ethylene or trimethylene; and Q is 2-oxetanyl, 3-oxetanyl, 2-tetrahydrofuranyl, 3-tetrahydrofuranyl, 1, 3-dioxolan-2-yl, 1,3-dioxolan-4-yl, 1,3-dioxan-2-yl, 1,3-dioxan-4-yl or 1,3-dioxan-5-yl;

or a pharmaceutically-acceptable salt thereof.

A further preferred compound of the invention is a quinazoline derivative of the formula I wherein $(R^2)_n$ is 3'-chloro-4'-fluoro;

$R^1$ is methoxy;

A is methylene or ethylene; and Q is 3-oxetanyl, 2-tetrahydrofuranyl, 1,3-dioxolan-2-yl, 1,3-dioxolan-4-yl, 1,3-dioxan-2-yl or 1,3-dioxan-5-yl;

or a pharmaceutically-acceptable salt thereof.

A specific preferred compound of the invention is the quinazoline derivative of the formula I: 4-(3'-chloro-4'-fluoroanilino)-7-methoxy-6-tetrahydrofuran-2-ylmethoxyquinazoline, 4-(3'-chloro-4'-fluoroanilino)-6-(1,3-dioxolan-2-ylmethoxy)-7-methoxyquinazoline, 4-(3'-chloro-4'-fluoroanilino)-6-[2-(1,3-dioxolan-2-yl)ethoxy]-7-methoxyquinazoline, 4-(3'-chloro-4'-fluoroanilino)-6-[3-(1,3-dioxolan-2-yl)propoxy]-7-methoxyquinazoline, 4-(3'-chloro-4'-fluoroanilino)-6-(1,3-dioxolan-4-ylmethoxy)-7-methoxyquinazoline, 4-(3'-chloro-4'-fluoroanilino)-6-[(4R)-2,2-dimethyl-1,3-dioxolan-4-ylmethoxy]-7-methoxyquinazoline, 4-(3'-chloro-4'-fluoroanilino)-6-[(4S)-2,2-dimethyl- 1,3-dioxolan-4-ylmethoxy]-7-methoxyquinazoline, 4-(3'-chloro-4'-fluoroanilino)-6-[2-(1,3-dioxan-2-yl)ethoxy]-7-methoxyquinazoline, 4-(3'-chloro-4'-fluoroanilino)-7-methoxy-6-(5-methyl- 1,3-dioxan-5-ylmethoxy) quinazoline or 4-(3'-chloro-4'-fluoroanilino)-7-methoxy-6-(3-methyloxetan-3-ylmethoxy)quinazoline; or a pharmaceutically-acceptable salt thereof.

A quinazoline derivative of the formula I, or a pharmaceutically-acceptable salt thereof, may be prepared by any process known to be applicable to the preparation of chemically-related compounds. Suitable processes include, for example, those illustrated in European Patent Applications Nos. 0520722, 0566226, 0602851, 0635498 and 0635507, and International Patent Applications WO 96/15118 and WO 96/16960. Such processes, when used to prepare a quinazoline derivative of the formula I, or a pharmaceutically-acceptable salt thereof, are provided as a further feature of the invention and are illustrated by the following representative examples in which, unless otherwise stated, n, $R^2$, $R^1$, A and Q have any of the 5 meanings defined hereinbefore for a quinazoline derivative of the formula I. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

(a) The reaction, conveniently in the presence of a suitable base, of a quinazoline of the formula II

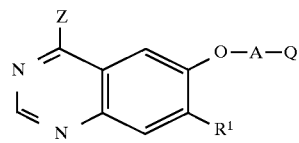

wherein Z is a displaceable group, with an aniline of the formula III

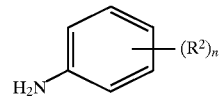

A suitable displaceable group Z is, for example, a halogeno, alkoxy, aryloxy or sulphonyloxy group, for example a chloro, bromo, methoxy, phenoxy, methanesulphonyloxy or toluene-4-sulphonyloxy group.

A suitable base is, for example, an organic amine base such as, for example, pyridine, 2,6-lutidine, collidine, 4-dimethylaminopyridine, triethylamine, morpholine, N-methylmorpholine or diazabicyclo [5.4.0]undec-7-ene, or, for example, an alkali or alkaline earth metal carbonate or hydroxide, for example sodium carbonate, potassium carbonate, calcium carbonate, sodium hydroxide or potassium hydroxide. Alternatively a suitable base is, for example, an alkali metal or alkaline earth metal amide, for example sodium amide or sodium bis(trimethylsilyl)amide.

The reaction is preferably carried out in the presence of a suitable inert solvent or diluent, for example an alkanol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10° to 150° C., preferably in the range 20° to 80° C.

The quinazoline derivative of the formula I may be obtained from this process in the form of the free base or alternatively it may be obtained in the form of a salt with the acid of the formula H-Z wherein Z has the meaning defined hereinbefore. When it is desired to obtain the free base from the salt, the salt may be treated with a suitable base as defined hereinbefore using a conventional procedure.

(b) The alkylation, conveniently in the presence of a suitable base as defined hereinbefore, of a quinazoline derivative of the formula IV

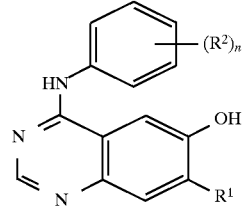

with an alkylating agent of the formula Z-A-Q wherein Z is a displaceable group as defined hereinbefore.

The reaction is preferably carried out in the presence of a suitable inert solvent or diluent as defined hereinbefore and at a temperature in the range, for example, 10° to 140° C., conveniently at or near ambient temperature or at or near 80° C.

When a pharmaceutically-acceptable salt of a quinazoline derivative of the formula I is required, for example a mono- or di-acid-addition salt of a quinazoline derivative of the formula I, it may be obtained, for example, by reaction of said compound with, for example, a suitable acid using a conventional procedure.

As stated hereinbefore the quinazoline derivatives defined in the present invention possess anti-proliferative activity which is believed to arise from the Class I receptor tyrosine kinase inhibitory activity of the compounds. These properties may be assessed, for example, using one or more of the procedures set out below:

(a) An in vitro assay which determines the ability of a test compound to inhibit the enzyme EGF receptor tyrosine kinase. Receptor tyrosine kinase was obtained in partially purified form from A-431 cells (derived from human vulval carcinoma) by the procedures described below which are related to those described by Carpenter et al, J. Biol. Chem., 1979, 254, 4884, Cohen et al, J. Biol. Chem., 1982, 257, 1523 and by Braun et al., J. Biol. Chem., 1984, 259, 2051.

A-431 cells were grown to confluence using Dulbecco's modified Eagle's medium (DMEM) containing 5% fetal calf serum (FCS). The obtained cells were homogenised in a hypotonic borate/EDTA buffer at pH 10.1. The homogenate was centrifuged at 400 g for 10 minutes at 0°–4° C. The supernatant was centrifuged at 25,000 g for 30 minutes at 0°–4° C. The pelleted material was suspended in 30 mM Hepes buffer at pH 7.4 containing 5% glycerol, 4 mM benzamidine and 1% Triton X-100, stirred for 1 hour at 0°–4° C., and recentrifuged at 100,000 g for 1 hour at 0°–4° C. The supernatant, containing solubilised receptor tyrosine kinase, was stored in liquid nitrogen.

For test purposes 40 µl of the enzyme solution so obtained was added to a mixture of 400 µl of a mixture of 150 mM Hepes buffer at pH 7.4, 500 µM sodium orthovanadate, 0.1% Triton X-100, 10% glycerol, 200 µl water, 80 µl of 25 mM DTT and 80 µl of a mixture of 12.5 mM manganese chloride, 125 mM magnesium chloride and distilled water. There was thus obtained the test enzyme solution.

Each test compound was dissolved in dimethylsulphoxide (DMSO) to give a 50 mM solution which was diluted with 40 mM Hepes buffer containing 0.1% Triton X-100, 10% glycerol and 10% DMSO to give a 500 µM solution. Equal volumes of this solution and a solution of epidermal growth factor (EGF; 20 µg/ml) were mixed.

[γ-$^{32}$P]ATP (3000 Ci/mM, 250 µCi) was diluted to a volume of 2 ml by the addition of a solution of ATP (100 µM) in distilled water. An equal volume of a 4 mg/ml solution of the peptide Arg-Arg-Leu-Ile-Glu-Asp-Ala-Glu-Tyr-Ala-Ala-Arg-Gly in a mixture of 40 mM Hepes buffer at pH 7.4, 0.1% Triton X-100 and 10% glycerol was added.

The test compound/EGF mixture solution (5 µl) was added to the test enzyme solution (10 µl) and the mixture was incubated at 0°–4° C. for 30 minutes. The ATP/peptide mixture (10 µl) was added and the mixture was incubated at 25° C. for 10 minutes. The phosphorylation reaction was terminated by the addition of 5% trichloroacetic acid (40 µl) and bovine serum albumin (BSA; 1 mg/ml, 5 µl). The mixture was allowed to stand at 4° C. for 30 minutes and then centrifuged. An aliquot (40 µl) of the supernatant was placed onto a strip of Whatman p 81 phosphocellulose paper. The strip was washed in 75 mM phosphoric acid (4×10 ml) and blotted dry. Radioactivity present in the filter paper was measured using a liquid scintillation counter (Sequence A). The reaction sequence was repeated in the absence of the EGF (Sequence B) and again in the absence of the test compound (Sequence C).

Receptor tyrosine kinase inhibition was calculated as follows:

$$\% \text{ Inhibition} = \frac{100 - (A - B)}{C - B} \times 100$$

The extent of inhibition was then determined at a range of concentrations of test compound to give an IC$_{50}$ value.

(b) An in vitro assay which determines the ability of a test compound to inhibit the EGF-stimulated growth of the human naso-pharyngeal cancer cell line KB.

KB cells were seeded into wells at a density of 1×10$^4$-1.5×10$^4$ cells per well and grown for 24 hours in DMEM supplemented with 5% FCS (charcoal-stripped). Cell growth was determined after incubation for 3 days by the extent of metabolism of MTT tetrazolium dye to furnish a bluish colour. Cell growth was then determined in the presence of EGF (10 ng/ml) or in the presence of EGF (10 ng/ml) and a test compound at a range of concentrations. An IC$_{50}$ value could then be calculated.

(c) An in-vivo assay in a group of athymic nude mice (strain ONU:Alpk) which determines the ability of a test compound (usually administered orally as a ball-milled suspension in 0.5% polysorbate) to inhibit the growth of xenografts of the human vulval epidermoid carcinoma cell line A-431.

A-431 cells were maintained in culture in DMEM supplemented with 5% FCS nd 2 mM glutamine. Freshly cultured cells were harvested by trypsinization and injected subcutaneously (10 million cells/0.1 ml/mouse) into both flanks of a number of donor nude mice. When sufficient tumour material was available (after approximately 9 to 14 days), fragments of tumour tissue were transplanted in the flanks of recipient nude mice (test day 0). Generally, on the seventh day after transplantation (test day 7) groups of 7 to 10 mice with similar-sized tumours were selected and dosing of the test compound was commenced. Once daily dosing of test compound was continued for a total of 13 days (test days 7 to 19 inclusive). In some studies the dosing of the test compound was continued beyond test day 19, for example to test day 26. In each case, on the following test day the animals were killed and the final tumour volume was calculated from measurements of the length and width of the tumours. Results were calculated as a percentage inhibition of tumour volume relative to untreated controls.

Although the pharmacological properties of the compounds of the formula I vary with structural change as expected, in general activity possessed by compounds of the formula I may be demonstrated at the following concentrations or doses in one or more of the above tests (a), (b) and (c):

Test (a): IC$_{50}$ in the range, for example, 0.005–0.1 µM;

Test (b): IC$_{50}$ in the range, for example, 0.02–1 µM;

Test (c): inhibition of tumour volume from a daily dose in the range, for example, 50 to 200 mg/kg.

Thus, by way of example, the compounds described in the accompanying Examples possess activity at approximately the following concentrations or doses in tests (a) and (b).

| Example | Test (a) IC$_{50}$ (µM) | Test (b) IC$_{50}$ (µM) |
|---|---|---|
| 1 | 0.08 | 0.15, 0.25, 0.54 |
| 2 | 0.01 | 0.2 |
| 3 | 0.01 | 0.33 |

| Example | Test (a) IC$_{50}$ ($\mu$M) | Test (b) IC$_{50}$ ($\mu$M) |
|---|---|---|
| 4 | 0.04 | 0.14 |
| 5 | 0.015 | 0.14 |
| 6 | 0.01 | 0.13 |
| 7 | 0.08 | 0.07 |
| 8 | 0.005 | 0.04 |
| 9 | 0.07 | 0.5 |
| 10 | 0.01, 0.034 | 0.065 |

In addition the compound described in Example 3 hereinafter possesses activity in test (c) with an ED$_{50}$ value of approximately 50 mg/kg.

According to a further aspect of the invention there is provided a pharmaceutical composition which comprises a quinazoline derivative of the formula I, or a pharmaceutically-acceptable salt thereof, as defined hereinbefore in association with a pharmaceutically-acceptable diluent or carrier.

The composition may be in a form suitable for oral administration, for example as a tablet or capsule, for parenteral injection (including intraveous, subcutaneous, intramuscular intravascular or infusion) as a sterile solution, suspension or emulsion, for topical administration as an ointment or cream or for rectal administration as a suppository.

In general the above compositions may be prepared in a conventional manner using conventional excipients.

The quinazoline derivative will normally be administered to a warm-blooded animal at a unit dose within the range 5–10000 mg per square meter body area of the animal, i.e. approximately 0.1–200 mg/kg, and this normally provides a therapeutically-effective dose. A unit dose form such as a tablet or capsule will usually contain, for example 1–250 mg of active ingredient. Preferably a daily dose in the range of 1–100 mg/kg is employed. For the quinazoline derivative of Example 3, or a pharmaceutically-acceptable salt thereof, a daily dose of approximately 1 to 40 mg/kg, preferably of 1 to 10 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a quinazoline derivative of the formula I as defined hereinbefore for use in a method of treatment of the human or animal body by therapy.

We have found that the compounds of the present invention possess anti-proliferative properties such as anti-cancer properties which are believed to arise from their Class I (EGF type) receptor tyrosine kinase inhibitory activity. Accordingly the compounds of the present invention are expected to be useful in the treatment of diseases or medical conditions mediated alone or in part by Class I receptor tyrosine kinases, i.e. the compounds may be used to produce a Class I receptor tyrosine kinase inhibitory effect in a warm-blooded animal in need of such treatment. Thus the compounds of the present invention provide a method for treating the proliferation of malignant cells characterised by inhibition of Class I receptor tyrosine kinases, i.e. the compounds may be used to produce an anti-proliferative effect mediated alone or in part by the inhibition of Class I receptor tyrosine kinase. Accordingly the compounds of the present invention are expected to be useful in the treatment of psoriasis and/or cancer by providing an anti-proliferative effect, particularly in the treatment of Class I receptor tyrosine kinase sensitive cancers such as cancers of the breast, lung, colon, rectum, stomach, prostate, bladder, pancreas and ovary.

Thus according to this aspect of the invention there is provided the use of a quinazoline derivative of the formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative as defined immediately above.

As stated above the size of the dose required for the therapeutic or prophylactic treatment of a particular proliferative disease will necessarily be varied depending on the host treated, the route of administration and the severity of the illness being treated. A unit dose in the range, for example, 1–200 mg/kg, preferably 1–100 mg/kg, more preferably 1–10 mg/kg is envisaged.

The anti-proliferative treatment defined hereinbefore may be applied as a sole therapy or may involve, in addition to the quinazoline derivative of the invention, surgery, conventional radiotherapy or one or more other anti-tumour substances, for example cytotoxic or cytostatic anti-tumour substances, for example those selected from, for example, tyrosine kinase inhibitors, serine/threonine kinase inhibitors, mitotic inhibitors, for example vinblastine, vindesine and vinorelbine; tubulin disassembly inhibitors such as taxol and taxotere; alkylating agents, for example cis-platin, carboplatin and cyclophosphamide; antimetabolites, for example 5-fluorouracil, tegafur, methotrexate, cytosine arabinoside and hydroxyurea, or, for example, one of the preferred antimetabolites disclosed in European Patent Application No. 239362 such as N-{5-[N-(3, 4-dihydro-2-methyl-4-oxoquinazolin-6-ylmethyl)-N-methylamino]-2-thenoyl}-L-glutamic acid; intercalating antibiotics, for example adriamycin, mitomycin and bleomycin; enzymes, for example asparaginase; topoisomerase inhibitors, for example etoposide and camptothecin; biological response modifiers, for example interferon; anti-hormones, for example antioestrogens such as tamoxifen, toremifene or raloxifene, for example antiandrogens such as 4'-cyano-3-(4-fluorophenylsulphonyl)-2-hydroxy-2-methyl-3'-(trifluoromethyl)-propionanilide (bicalutamide), flutamide, nilutamide or cyproterone acetate, or, for example LHRH antagonists or LHRH agonists such as goserelin, leuprorelin or buserelin and hormone synthesis inhibitors, for example aromatase inhibitors such as those disclosed in European Patent Application No. 0296749, for example 2,2'-[5-(1H-1,2,4-triazol-1-ylmethyl)-1,3-phenylene]bis(2-methylpropionitrile) (anastrozole), letrazole or vorazole, and, for example, inhibitors of 5α-reductase such as 17β-(N-tert-butylcarbamoyl)-4-aza-5α-androst-1-en-3-one (finasteride). Such conjoint treatment may be achieved by way of the simultaneous, sequential or separate dosing of the individual components of the treatment. According to this aspect of the invention there is provided a pharmaceutical product comprising a quinazoline derivative of the formula I as defined hereinbefore and an additional anti-tumour substance as defined hereinbefore for the conjoint treatment of cancer.

As stated above the quinazoline derivative defined in the present invention is an effective anti-cancer agent, which property is believed to arise from its Class I (EGF type) receptor tyrosine kinase inhibitory properties. Such a quinazoline derivative of the invention is expected to possess a wide range of anti-cancer properties as Class I receptor tyrosine kinases have been implicated in many common human cancers such as leukaemia and breast, lung, colon, rectal, stomach, prostate, bladder, pancreas and ovarian cancer. Thus it is expected that a quinazoline derivative of the invention will possess anti-cancer activity against these cancers. It is in addition expected that a quinazoline derivative of the present invention will possess activity against a range of leukaemias, lymphoid malignancies and solid tumours such as carcinomas and sarcomas in tissues such as the liver, kidney, prostate and pancreas.

It is further expected that a quinazoline derivative of the invention will possess activity against other diseases involving excessive cellular proliferation such as psoriasis and benign prostatic hypertrophy, atherosclerosis and restenosis.

It is also to be expected that a quinazoline derivative of the invention will be useful in the treatment of additional disorders of cellular growth in which aberrant cell signalling by way of receptor tyrosine kinase enzymes or non-receptor tyrosine kinase enzymes, including as yet unidentified tyrosine kinase enzymes, are involved. Such disorders include, for example, inflammation, angiogenesis, vascular restenosis, immunological disorders, pancreatitis, kidney disease and blastocyte maturation and implantation.

The invention will now be illustrated in the following non-limiting Examples in which, unless otherwise stated:

(i) evaporations were carried out by rotary evaporation in vacuo and work-up procedures were carried out after removal of residual solids such as drying agents by filtration, unless otherwise stated magnesium sulphate was used as a drying agent for organic solutions;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet, unless otherwise stated end-products of the formula I were dissolved in $CD_3SOCD_3$ for the determination of NMR values;

(vii) intermediates were not generally fully characterised and purity was assessed by thin layer chromatography (TLC), infra-red (IR) or NMR analysis;

(viii) the following abbreviations have been used:

| | |
|---|---|
| DMF | N,N-dimethylformamide; |
| DMSO | dimethylsulphoxide. |

EXAMPLE 1

A mixture of 4-(3'-chloro-4'-fluoroanilino)-6-hydroxy-7-methoxyquinazoline (1.28 g), 2-bromomethyltetrahydrofuran (0.67 g), potassium carbonate (2.8 g) and DMF (20 ml) was stirred and heated to 80° C. for 6 hours. The mixture was evaporated and the residue was partitioned between ethyl acetate and water. A precipitate was deposited. The solid was isolated. The organic phase was separated, washed with water and with brine, dried ($MgSO_4$) and evaporated. The residue was purified by column chromatography using initially a 50:1 mixture and then a 20:1 mixture of methylene chloride and methanol as eluent. The solid so obtained was combined with the precipitate which had been isolated previously and recrystallised from ethanol. There was thus obtained 4-(3'-chloro-4'-fluoroanilino)-7-methoxy-6-tetrahydrofuran-2-ylmethoxyquinazoline (0.5 g), m.p. 145°–146° C.; NMR Spectrum: 1.74 (m, 1H), 1.91 (m, 2H), 2.07 (m, 1H), 3.7 (m, 1H), 3.82 (m, 1H), 3.92 (s, 3H), 4.08 (d, 2H), 4.26 (m, 1H), 7.18 (s, 1H), 7.43 (t, 1H), 7.77 (m, 2H), 8.1 (m, (s, 1H), 9.5 (s, 1H); Elemental Analysis: Found C, 59.4; H, 4.7; N, 10.3; $C_{20}H_{19}ClFN_3O_3$ requires C, 59.5; H, 4.7; N, 10.4%.

The 4-(3'-chloro-4'-fluoroanilino)-6-hydroxy-7-methoxyquinazoline used as a starting material was obtained as follows:

6,7-Dimethoxy-3,4-dihydroquinazolin-4-one (European Patent Application No. 0 566 226, Example 1 thereof; 26.5 g) was added portionwise to stirred methanesulphonic acid (175 ml). L-Methionine (22 g) was added and the resultant mixture was stirred and heated to reflux for 5 hours. The mixture was cooled to ambient temperature and poured onto a mixture (750 ml) of ice and water. The mixture was neutralised by the addition of a concentrated (40%) aqueous sodium hydroxide solution. The precipitate was isolated, washed with water and dried. There was thus obtained 6-hydroxy-7-methoxy-3,4-dihydroquinazolin-4-one (11.5 g).

After repetition of the previous reaction, a mixture of 6-hydroxy-7-methoxy-3,4-dihydroquinazolin-4-one (14.18 g), acetic anhydride (110 ml) and pyridine (14 ml) was stirred and heated to 100° C. for 2 hours. The mixture was poured onto a mixture (200 ml) of ice and water. The precipitate was isolated, washed with water and dried. There was thus obtained 6-acetoxy-7-methoxy-3,4-dihydroquinazolin-4-one (13 g, 75%);

NMR Spectrum: 2.3 (s, 3H), 3.8 (s, 3H), 7.3 (s, 1H), 7.8 (s, 1H), 8.1 (s, 1H), 12.2 (broad s, 1H).

After repetition of the previous steps, a mixture of 6-acetoxy-7-methoxy-3,4-dihydroquinazolin-4-one (15 g), thionyl chloride (215 ml) and DMF (4.3 ml) was stirred and heated to 90° C. for 4 hours. The mixture was cooled to ambient temperature and the thionyl chloride was evaporated. There was thus obtained 6-acetoxy-4-chloro-7-methoxyquinazoline, hydrochloride salt, which was used without further purification.

A mixture of the material so obtained, 3-chloro-4-fluoroaniline (9.33 g) and isopropanol (420 ml) was stirred and heated to 90° C. for 5 hours. The mixture was cooled to ambient temperature and the precipitate was isolated, washed in turn with isopropanol and methanol and then dried. There was thus obtained 6-acetoxy-4-(3'-chloro-4'-fluoroanilino)-7-methoxyquinazoline hydrochloride salt (14 g, 56%); NMR Spectrum: 2.4 (s, 3H), 4.0 (s, 3H), 7.5 (t, 1H), 7.6 (s, 1H), 7.75 (m, 1H), 8.05 (m 1H, 8.8 (s, 1H), 8.95 (s, 1H), 11.5 (broad s, 1H).

A concentrated aqueous ammonium hydroxide solution (30% weight/volume, 7.25 ml) was added to a stirred mixture of the material so obtained and methanol (520 ml). The mixture was stirred at ambient temperature for 17 hours and then heated to 100° C. for 1.5 hours. The mixture was cooled and the precipitate was isolated and dried. There was thus obtained 4-(3'-chloro-4'-fluoroanilino)-6-hydroxy-7-methoxyquinazoline (10.62 g, 95%), m.p. >270° C. (decomposes); NMR Spectrum: 4.0 (s, 3H), 7.2 (s, 1H), 7.4 (t, 1H), 7.8 (s, 1H), 7.85 (m, 1H), 8.2 (m, 1H), 8.5 (s, 1H), 9.45 (s, 1H), 9.65 (s, 1H).

EXAMPLE 2

4-(3'-Chloro-4'-fluoroanilino)-6-hydroxy-7-methoxyquinazoline (1.3 g) was added to a stirred mixture of powdered potassium hydroxide (1.3 g) and DMSO (20 ml) and the mixture was stirred at ambient temperature for 30 minutes. 2-Bromomethyl-1,3-dioxolane (0.83 ml) was added and the mixture was stirred at ambient temperature for 72 hours. The mixture was partitioned between ethyl acetate (containing 5% 1-butanol) and water. The organic phase was washed with water and evaporated. The residue was purified by column chromatography using initially a 50:1 mixture and then a 20:1 mixture of methylene chloride and methanol as eluent. The resultant oil crystallised on standing and was recrystallised from acetonitrile. There was thus obtained 4-(3'-chloro-4'-fluoroanilino)-6-(1,3-dioxolan-2-ylmethoxy)-7-methoxyquinazoline (0.24 g), m.p. 145–146° C.; NMR Spectrum: 3.94 (s, 3H), 3.98 (m, 4H), 4.15 (d, 2H), 5.34 (t, 1H), 7.2 (s, 1H), 7.42 (t, 1H), 7.8 (m, 2H), 8.11 (m, 1H), 8.49 (s, 1H), 9.49 (s, 1H); Elemental Analysis: Found C, 54.1; H, 4.6; N, 10.1; $C_{19}H_{17}ClFN_3O_4 1H_2O$ requires C, 53.9; H, 4.5; N, 9.9%.

EXAMPLE 3

Using an analogous procedure to that described in Example 2, 4-(3'-chloro-4'-fluoroanilino)-6-hydroxy-7-methoxyquinazoline was reacted with 2-(2-bromoethyl)-1,3-dioxolane to give 4-(3'-chloro-4'-fluoroanilino)-6-[2-(1,3-dioxolan-2-yl)ethoxy]-7-methoxyquinazoline in 29% yield, m.p. 167°–168° C. (recrystallised from ethanol); NMR Spectrum: 2.16 (m, 2H), 3.87 (m, 4H), 3.94 (s, 3H), 4.25 (t, 2H), 5.06 (t, 1H), 7.2 (s, 1H), 7.43 (t, 1H), 7.8 (m, 2H), 8.12 (m, 1H), 8.49 (s, 1H), 9.53 (s, 1H); Elemental Analysis: Found C, 55.2; H, 4.9; N, 9.6; $C_{20}H_{19}ClFN_3O_4 1H_2O$ requires C, 54.9; H, 4.8; N, 9.6%.

EXAMPLE 4

Using an analogous procedure to that described in Example 2, 4-(3'-chloro-4'-fluoroanilino)-6-hydroxy-7-methoxyquinazoline was reacted with 2-(3-chloropropyl)-1,3-dioxolane to give 4-(3'-chloro-4'-fluoroanilino)-6-[3-(1,3-dioxolan-2-yl)propoxy]-7-methoxyquinazoline in 54% yield, m.p. 170°–171° C. (recrystallised from ethanol); NMR Spectrum: 1.8 (m, 2H), 1.92 (m, 2H), 3.85 (m, 4H), 3.95 (s, 3H), 4.17 (t, 2H), 4.9 (t, 1H), 7.2 (s, 1H), 7.42 (t, 1H), 7.78 (m, 2H), 8.12 (m, 1H), 8.5 (s, 1H), 9.5 (s, 1H); Elemental Analysis: Found C, 57.6; H, 4.9; N, 9.5; $C_{21}H_{21}ClFN_3O_4 0.2H_2O$ requires C, 57.7; H, 4.9; N, 9.6%.

EXAMPLE 5

A mixture of 4-(3'-chloro-4'-fluoroanilino)-6-hydroxy-7-methoxyquinazoline (1.28 g), 4-(4-toluenesulphonyloxymethyl)-1,3-dioxolane (Let. Lett., 1993, 34, 4335, 2.1 g), potassium carbonate (2.8 g) and DMSO (20 ml) was stirred at ambient temperature for 16 hours. The mixture was partitioned between ethyl acetate and water. The organic phase was washed with water and with brine, dried ($Na_2SO_4$) and evaporated. The residue was purified by column chromatography using a 20:1 mixture of methylene chloride and methanol as eluent. There was thus obtained 4-(3'-chloro-4'-fluoroanilino)-6-(1,3-dioxolan-4-ylmethoxy)-7-methoxyquinazoline (1.19 g), m.p. 214°–215° C. (recrystallised from acetonitrile); NMR Spectrum: 3.8 (m, 1H), 3.95 (s, 3H), 4.08 (m, 1H), 4.2 (m, 2H), 4.52 (m, 1H), 4.9 (s, 1H), 5.04 (s, 1H), 7.22 (s, 1H), 7.45 (t, 1H), 7.8 (m, 2H), 8.13 (m, 1H), 8.52 (s, 1H), 9.5 (s, 1H; Elemental Analysis: Found C, 56.3; H, 4.2; N, 10.6; $C_{19}H_{17}ClFN_3O_4$ requires C, 56.2; H, 4.2; N, 10.4%.

EXAMPLE 6

Using an analogous procedure to that described in Example 1, 4-(3'-chloro-4'-fluoroanilino)-6-hydroxy-7-methoxyquinazoline was reacted with (4S)-2,2-dimethyl-4-(4-toluenesulphonyloxymethyl)-1,3-dioxolane to give 4-(3'-chloro-4'-fluoroanilino)-6-[(4R)-2,2-dimethyl-1,3-dioxolan-4-ylmethoxy]-7-methoxyquinazoline in 57% yield; NMR Spectrum: 1.35 (s, 3H), 1.42 (s, 3H), 3.85 (m, 1H), 3.96 (s, 3H), 4.2 (m, 3H), 4.55 (m, 1H), 7.21 (s, 1H), 7.44 (t, 1H), 7.8 (m, 2H), 8.12 (m, 1H), 8.5 (s, 1H), Elemental Analysis: Found C, 58.1; H, 4.6; N, 9.5; $C_{21}H_{21}ClFN_3O_4$ requires C, 58.1; H, 4.9; N, 9.7%.

EXAMPLE 7

Using an analogous procedure to that described in Example 1, 4-(3'-chloro-4'-fluoroanilino)-6-hydroxy-7-methoxyquinazoline was reacted with (4R)-2,2-dimethyl-4-(4-toluenesulphonyloxymethyl)-1,3-dioxolane to give 4-(3'-chloro-4'-fluoroanilino)-6-[(4S)-2,2-dimethyl-1,3-dioxolan-4-ylmethoxy]-7-methoxyquinazoline in 50% yield; NMR Spectrum: 1.35 (s, 3H), 1.42 (s, 3H), 3.85 (m, 1H), 3.95 (s, 3H), 4.18 (m, 3H), 4.53 (m, 1H), 7.2 (s, 1H), 7.42 (t, 1H), 7.8 (m, 2H), 8.12 (m, 1H), 8.48 (s, 1H), 9.48 (s, 1H); Elemental Analysis: Found C, 58.6; H, 4.9; N, 9.7; $C_{21}H_{21}ClFN_3O_4$ requires C, 58.1; H, 4.9; N, 9.7%.

EXAMPLE 8

Using an analogous procedure to that described in Example 1, 4-(3'-chloro-4'-fluoroanilino)-6-hydroxy-7-methoxyquinazoline was reacted with 2-bromoethyl-1,3-dioxane to give 4-(3'-chloro-4'-fluoroanilino)-6-[2-(1,3-dioxan-2-yl)ethoxy]-7-methoxyquinazoline in 30% yield; NMR Spectrum: 1.38 (m, 1H), 1.72 (m, 1H), 2.08 (q, 2H), 3.76 (m, 2H), 3.95 (s, 3H), 4.04 (m, 2H), 4.2 (t, 2H), 4.8 (t, 1H), 7.21 (s, 1H), 7.44 (t, 1H), 7.8 (m, 2H), 8.5 (s, 1H), 8.56 (s, 1H); Elemental Analysis: Found C, 55.9; H, 4.7; N, 9.2; $C_{21}H_{21}ClFN_3O_4 1H_2O$ requires C, 55.8; H, 5.1; N, 9.3%.

EXAMPLE 9

Using an analogous procedure to that described in Example 5, 4-(3'-chloro-4'-fluoroanilino)-6-hydroxy-7-methoxyquinazoline was reacted with 5-methyl-5-(4-toluenesulphonyloxymethyl)-1,3-dioxane to give 4-(3'-chloro-4'-fluoroanilino)-7-methoxy-6-(5-methyl-1,3-dioxan-5-ylmethoxy)quinazoline in 42% yield, m.p. 212°–213° C. (recrystallised from ethanol and dried under vacuum at 70° C.); NMR Spectrum: 0.93 (s, 3H), 3.53 (d, 2H), 3.93 (m, 5H), 4.19 (s, 2H), 4.68 (d, 1H), 4.93 (d, 1H), 7.2 (s, 1H), 7.43 (t, 1H), 7.77 (m, 1H), 7.87 (s, 1H), 8.1 (m, 1H), 8.48 (s, 1H), 9.58 (s, 1H); Elemental Analysis: Found C, 58.1; H, 4.8; N, 9.7; $C_{21}H_{21}ClFN_3O_4$ requires C, 58.1; H, 4.9; N, 9.7%.

The 5-methyl-5-(4-toluenesulphonyloxymethyl)-1,3-dioxane used as a starting material was obtained as follows:
4-Toluenesulphonyl chloride (19.05 g) was added to a stirred mixture of 5-hydroxymethyl-5-methyl-1,3- dioxan (13.2 g) and pyridine (200 ml) and the resultant mixture was stirred at ambient temperature for 20 hours. The mixture was filtered and the filtrate was evaporated. The residue was partitioned between ethyl acetate and water. The organic phase was washed with a 1M aqueous hydrochloric acid solution and with brine, dried (MgSO$_4$) and evaporated. There was thus obtained the required starting material (21.3 g), m.p. 86°–88° C.

EXAMPLE 10

Using an analogous procedure to that described in Example 5 except that the reaction mixture was stirred at ambient temperature for 72 hours, 4-(3'-chloro-4'-fluoroanilino)-6-hydroxy-7-methoxyquinazoline was reacted with 3-methyl-3-(4-toluenesulphonyloxymethyl)-oxetane (Chem. Pharm. Bull., 1985, 33, 1707) to give 4-(3'-chloro-4'-fluoroanilino)-7-methoxy-6-(3-methyloxetan-3-ylmethoxy)quinazoline in 24% yield, m.p. 226°–227° C. (recrystallised from ethanol); NMR Spectrum: 1.43 (s, 3H), 3.93 (s, 3H), 4.23 (s, 2H), 4.37 (d, 2H), 4.53 (d, 2H), 7.2 (s, 1H), 7.43 (t, 1H), 7.78 (m, 1H), 7.88 (s, 1H), 8.11 (m, 1H), 8.49 (s, 1H), 9.49 (s, 1H); Elemental Analysis: Found C, 59.5; H, 4.7; N, 10.2; C$_{20}$H$_{19}$ClFN$_3$O$_3$ requires C, 59.5; H, 4.7; N, 10.4%.

EXAMPLE 11

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur. | 223.75 |
| Croscarmellose sodium | 6.0 |
| Maize starch | 15.0 |
| Polyvinylpyrrolidone | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur. | 488.5 |
| Magnesium stearate | 1.5 |

| (e) Injection I | (50 mg/ml) |
|---|---|
| Compound X | 5.0% w/v |
| 1M Sodium hydroxide solution | 15.0% w/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1M Sodium hydroxide solution | 15.0% w/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

I claim:

1. A quinazoline derivative of the formula I

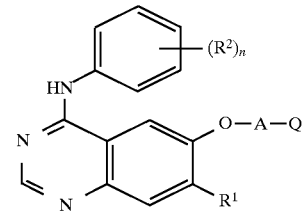

wherein n is 1,2 or 3 and each R$^2$ is independently halogeno, trifluoromethyl or (1-4C)alkyl;

R$^1$ is (1-4C)alkoxy;

A is (1-4C)alkylene; and

Q is a saturated, monocyclic 4-, 5-, 6- or 7-membered heterocyclic ring consisting of carbon atoms and one or two oxygen heteroatoms, which ring optionally bears up to four (1-4C)alkyl substituents; or a pharmaceutically-acceptable salt thereof.

2. A quinazoline derivative of the formula I as claimed in claim 1 wherein n is 1,2 or 3 and each R$^2$ is independently fluoro, chloro, bromo, trifluoromethyl or methyl.

3. A quinazoline derivative of the formula I as claimed in claim 1 wherein R$^1$ is methoxy or ethoxy and A is methylene, ethylene or trimethylene.

4. A quinazoline derivative of the formula I as claimed in claim 1 wherein Q is 2-oxetanyl, 3-oxetanyl, 2-tetrahydrofuranyl, 3-tetrahydrofuranyl, 1,3-dioxolan-2-yl, 1,3-dioxolan-4-yl, 1,3-dioxan-2-yl, 1,3-dioxan-4-yl or 1,3-dioxan-5-yl.

5. A quinazoline derivative of the formula I as claimed in claim 1 wherein (R$^2$)$_n$ is 3'-chloro, 3'-bromo, 3',4'-difluoro, 3',4'-dichloro, 3'-fluoro-4'-chloro or 3'-chloro-4'-fluoro;

R$^1$ is methoxy or ethoxy;

A is methylene, ethylene or trimethylene; and

Q is 2-oxetanyl, 3-oxetanyl, 2-tetrahydrofuranyl, 3-tetrahydrofuranyl, 1,3-dioxolan-2-yl, 1,3-dioxolan-4-yl, 1,3-dioxan-2-yl, 1,3-dioxan-4-yl or 1,3-dioxan-5-yl;

or a pharmaceutically-acceptable salt thereof.

6. A quinazoline derivative of the formula I as claimed in claim 1 wherein (R$^2$)$_n$ is 3'-chloro-4'-fluoro;

R$^1$ is methoxy;

A is methylene or ethylene; and

Q is 3-oxetanyl, 2-tetrahydrofuranyl, 1,3-dioxolan-2-yl, 1,3-dioxolan-4-yl, 1,3-dioxan-2-yl or -1,3-dioxan-5-yl;

or a pharmaceutically-acceptable salt thereof.

7. The quinazoline derivative of the formula I as claimed in claim 1 selected from: 4-(3'-chloro-4'-fluoroanilino)-7-methoxy-6-tetrahydrofuran-2-ylmethoxyquinazoline, 4-(3'-chloro-4'-fluoroanilino)-6-(1,3-dioxolan-2-ylmethoxy)-7-methoxyquinazoline, 4-(3'-chloro-4'-fluoroanilino)-6-[2-(1,3-dioxolan-2-yl)ethoxy]-7-methoxyquinazoline, 4-(3'-chloro-4'-fluoroanilino)-6-[3-(1,3-dioxolan-2-yl)propoxy]-7-methoxyquinazoline, 4-(3'-chloro-4'-fluoroanilino)-6-(1,3-dioxolan-4-ylmethoxy)-7-methoxyquinazoline, 4-(3'-chloro-4'-fluoroanilino)-6-[(4R)-2,2-dimethyl-1,3-dioxolan-4-ylmethoxy]-7-methoxyquinazoline, 4-(3'-chloro-4'-fluoroanilino)-6-[(4S)-2,2-dimethyl-1,3-dioxolan-4-ylmethoxy]-7-methoxyquinazoline, 4-(3'-chloro-4'-fluoroanilino)-6-[2-(1,3-dioxan-2-yl)ethoxy]-7-methoxyquinazoline, 4-(3'-chloro-4'-fluoroanilino)-7-methoxy-6-(5-methyl-1,3-dioxan-5-ylmethoxy)quinazoline and 4-(3'-chloro-4'-fluoroanilino)-7-methoxy-6-(3-methyloxetan-3-ylmethoxy)quinazoline; or a pharmaceutically-acceptable salt thereof.

8. A process for the preparation of a quinazoline derivative of the formula I, or a pharmaceutically-acceptable salt thereof, as claimed in any one of claims 1 to 7 which comprises:

(a) the reaction of a quinazoline of the formula II

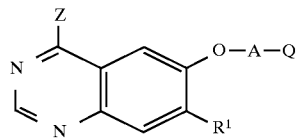

wherein Z is a displaceable group, with an aniline of the formula III

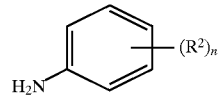

or (b) the alkylation of a quinazoline derivative of the formula IV

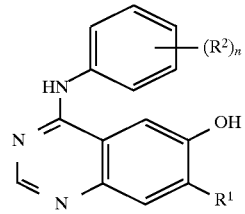

with an alkylating agent of the formula Z-A-Q wherein Z is a displaceable group;

and when a pharmaceutically-acceptable salt of a quinazoline derivative of the formula I is required, it may be obtained by reaction of said compound with a suitable acid using a conventional procedure.

9. A pharmaceutical composition which comprises a quinazoline derivative of the formula I, or a pharmaceutically-acceptable salt thereof, as claimed in any one of claims 1 to 7 in association with a pharmaceutically-acceptable diluent or carrier.

10. A method for producing an anti-proliferative effect in a warm-blooded animal, such as man, in need of such treatment which comprises administering to said animal an effective. amount of a quinazoline derivative, or a pharmaceutically-acceptable salt thereof, as claimed in any one of claims 1 to 7.

* * * * *

UNITED STATES PATENT AND TRADEMARK OFFICE
CERTIFICATE OF CORRECTION

PATENT NO. : 5,770,603
DATED : June 23, 1998
INVENTOR(S) : Gibson

Page 1 of 1

It is certified that error appears in the above-identified patent and that said Letters Patent is hereby corrected as shown below:

Title page,
Reads: "[22] Filed: April 10, 1997" should read -- [22] Filed: April 11, 1997 --

Signed and Sealed this

Twentieth Day of November, 2001

*Attest:*

*Attesting Officer*

NICHOLAS P. GODICI
*Acting Director of the United States Patent and Trademark Office*